(12) United States Patent
Tanaka et al.

(10) Patent No.: US 7,473,817 B1
(45) Date of Patent: Jan. 6, 2009

(54) ABSORBENT ARTICLE

(75) Inventors: Masahito Tanaka, Tochigi-ken (JP);
Mitsugu Hamajima, Tochigi-ken (JP);
Noriko Sakamoto, Tochigi-ken (JP);
Futoshi Teranishi, Tochigi-ken (JP);
Minoru Nakanishi, Tochigi-ken (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/573,893

(22) Filed: May 19, 2000

(30) Foreign Application Priority Data

May 20, 1999 (JP) .................................. 11-140652
Jan. 21, 2000 (JP) .............................. 2000-013558

(51) Int. Cl.
*A61F 13/15* (2006.01)
*B32B 27/12* (2006.01)
*B32B 5/18* (2006.01)
*B32B 5/24* (2006.01)
*B32B 5/26* (2006.01)

(52) U.S. Cl. ............... 604/358; 604/359; 604/365; 604/378; 604/385.23; 442/121; 442/370; 442/373; 442/381; 442/389

(58) Field of Classification Search .......... 442/121, 442/370, 373, 381, 389; 604/358, 359, 365, 604/378

See application file for complete search history.

(56) References Cited

U.S. PATENT DOCUMENTS

| 5,350,370 | A | * | 9/1994 | Jackson et al. ............... 604/374 |
| 5,429,628 | A | | 7/1995 | Trinh et al. |
| 5,582,603 | A | | 12/1996 | Difilippantonio et al. |
| 5,865,824 | A | * | 2/1999 | Chen et al. ............... 604/378 |
| 6,225,524 | B1 | * | 5/2001 | Guarracino et al. ......... 604/359 |
| 6,293,935 | B1 | * | 9/2001 | Kimura et al. ............... 604/387 |

FOREIGN PATENT DOCUMENTS

| EP | 0592001 A1 | 4/1997 |
| EP | 0811392 A1 | 12/1997 |
| JP | 58138452 | 8/1983 |
| JP | 59105448 | 6/1984 |
| JP | 2252555 | 10/1990 |
| JP | 5-277148 A | 10/1993 |
| JP | 8-508424 A | 9/1996 |
| WO | WO 94/22501 A1 | 10/1994 |

\* cited by examiner

*Primary Examiner*—Lynda Salvatore
(74) *Attorney, Agent, or Firm*—Birch, Stewart, Kolasch & Birch, LLP

(57) ABSTRACT

An absorbent article having a liquid permeable top layer, a liquid impermeable leakproof layer, and a liquid retentive absorbent layer interposed between the layers, wherein the absorbent layer has an odor-controlling member containing (a) 20 to 80% by weight of specific hydrophilic fiber or hydrophilic foam and (b) an odor-controlling agent, the odor-controlling member 9 being composed of a layer made up of a mutually dispersing mixture of component (a) and component (b) or being composed of adjacent layers separately comprising component (a) and component (b).

28 Claims, 1 Drawing Sheet

ABSORBENT ARTICLE

BACKGROUND OF THE INVENTION

The present invention relates to absorbent articles such as sanitary napkins, disposable diapers, adult incontinent pads, panty liners, underlaying sheets for pets, and the like. More particularly, the present invention relates to absorbent articles which have high odor-controlling effects and are resistant to the leakage of bad odors.

Absorbent articles having a deodorizing function are disclosed, e.g., in Japanese Patent Laid-Open Nos. 58-138452, 59-105448 and 2-252555. According to these conventional techniques, the deodorizing effect is not manifested as expected because hydrophilic materials such as paper and pulp are present around a deodorizing agent, and the absorbed liquid remains in these hydrophilic materials, enjoying little deodorizing effect.

In addition to the above prior arts, a number of attempts have been made to date to reduce the odor of menstrual blood by incorporating various deodorizing agents or aromatizing agents into the absorbent member, etc. of an absorbent article. The conventional absorbent articles aiming at deodorizing typically include the following three types:

(1) Those containing materials that adsorb and remove various odors, which are designed to perform a deodorizing function in a dry state (a state free of liquid).

(2) Those having a perfume contained in microcapsules, etc., which is released when wet on absorption of blood to exert a masking effect to thereby make the odor imperceptible.

(3) Those having improved breathability as a whole or containing an antimicrobial agent (bactericidal agent) to control growth of bacteria thereby suppressing the development or increase of odors from the metabolite of bacteria.

The products of type (1) are essentially to be effective for deodorizing but, in actual use, fail to fully enjoy the effect of deodorizing materials in the absence of considerations for the wet state of the products with body fluids, such as menstrual blood, so-called discharge (leukorrhea), and urine. The products of type (2) meet difficulty in making all odors imperceptible by masking. Moreover, the perfume can be released by moisture absorption during storage or can decompose with time causing it to lose its function. The products of type (3) are effective on ammonia that is generated on the decomposition of urine, as is observed with diapers and incontinence pads, but are ineffective on body fluids that give off strong odors immediately after being exuded, such as menstrual blood and other discharge. Further, the problem common to types (1) to (3) is that the products cannot sufficiently reduce all the odors of menstrual blood or discharge because the odors of these body fluids are composed of a variety of components and have high concentrations immediately after discharge.

SUMMARY OF THE INVENTION

Accordingly, an object of the present invention is to provide an absorbent article having high odor-controlling effects and resistance to the leakage of odors.

The object of the present invention is accomplished by an absorbent article comprising a liquid permeable top layer, a liquid impermeable leakproof layer, and a liquid retentive absorbent layer, wherein the absorbent layer has an odor-controlling member containing (a) hydrophilic fiber or hydrophilic foam which does not swell with water or a hydrophilic fiber or hydrophilic foam which has a centrifugal water retention of 0.7 g/g or less as measured after equilibrium water absorption and swelling followed by centrifugation and (b) an odor-controlling agent, the proportion of component (a) in the odor-controlling member being 20 to 80% by weight, and the odor-controlling member being composed of a layer made up of a mutually dispersing mixture of component (a) and component (b) or being composed of a layer comprising component (a) and a layer comprising component (b) which are adjacent to each other.

The above object of the present invention is also accomplished by an absorbent article used for body fluid absorption wherein, in tests which are carried out by introducing the following liquids into 900 mL glass containers respectively, immediately after the liquid introduction putting the absorbent articles into glass containers respectively, closing the glass containers tightly, and maintaining the closed glass containers at 25° C., the absorbent article is capable of reducing the concentration of:

ammonia gas to less than 10 ppm in 30 minutes and to 5 ppm or less in 3 hours in the case of introducing 0.1 μL of 29% by weight of an aqueous ammonia, and methyl mercaptan gas to 20 ppm or less in 30 minutes and to 2 ppm or less in 3 hours in the case of introducing 100 μL of a 1 μg/μL benzene solution of methyl mercaptan.

BRIEF DESCRIPTION OF THE DRAWINGS

The present invention will be more particularly described with reference to the accompanying drawings, in which.

DETAILED DESCRIPTION OF THE PREFERRED EMBODIMENTS

Figure 1:
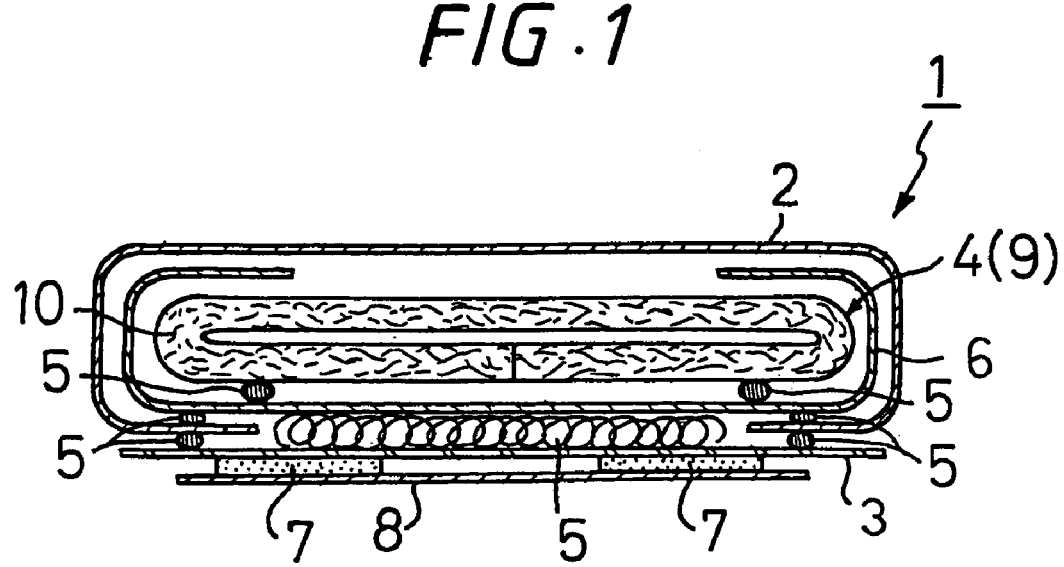
FIG. 1 is a cross-sectional view in the width direction of a sanitary napkin as an embodiment of the absorbent article according to the present invention.

The present invention will now be described based on the preferred embodiments thereof with reference to the accompanying drawings. FIG. 1 is a cross-sectional view in the width direction of a sanitary napkin 1 as an embodiment of the absorbent article according to the present invention. The sanitary napkin 1 shown in FIG. 1 has a substantially rectangular shape in its plan view and comprises a topsheet 2, serving as a liquid permeable top layer, a backsheet 3 serving as a liquid impermeable leakproof layer, and an absorbent member 4 serving as a liquid retentive absorbent layer which is interposed between the topsheet 2 and the backsheet 3. The absorbent member 4 is disposed on a leakproof sheet 6 with the back side of the absorbent member in contact with the leakproof sheet 6. The absorbent member 4 and the leakproof sheet 6 covering the back side of the absorbent member 4 are fixed together with a hot-melt adhesive 5. The leakproof sheet 6 extending from the lateral edges of the absorbent member 4 is folded toward the upper surface side to cover the lateral sides of the absorbent member 4. The topsheet 2 covers the upper side of the absorbent member 4. The topsheet 2 extending from the lateral edges of the absorbent member 4 is folded to the back side of the absorbent member 4 and fixed with a hot-melt adhesive 5 to the leakproof sheet 6 that covers the back side of the absorbent member 4. The hot-melt adhesive 5 is spirally applied to the outer side of the leakproof sheet 6 that covers the back side of the absorbent member 4. A hot-melt adhesive 5 is also applied to the outer side of the folded part of the topsheet 2 that is folded to the back side of the absorbent member 4. The backsheet 3, which serves as a leakproof layer, is bonded to the back side of the absorbent member 4 via the folded part of the topsheet 2 using the hot-melt adhesive 5. An adhesive 7 for fixing the napkin to the wearer's underwear is applied in two stripes on the outer side of the backsheet 3, and the adhesive 7 is covered with a release sheet 8. At the longitudinal front and rear edges of the absorbent member 4, which are not shown, the extending topsheet 2, the backsheet 3, and the leakproof sheet 6 are fixed together by heat-sealing. The above-described members making up the napkin 1 can be of conventional materials and structures.

The absorbent member 4 has an odor-controlling member 9. In this particular embodiment, the whole absorbent member 4 is an odor-controlling member 9. The odor-controlling member 9 (i.e., the absorbent member 4 in FIG. 1) contains (a) hydrophilic fiber or hydrophilic foam which does not swell with water or hydrophilic fibers or hydrophilic foam which has a water retention of 0.7 g/g or less after equilibrium water absorption and swelling followed by centrifugation (hereafter referred to as a centrifugal water retention) and (b) an odor-controlling agent.

When body fluids which give off unpleasant odors are absorbed by the napkin having an odor-controlling member containing components (a) and (b), the fluids are gathered toward the odor-controlling agent, with component (b) hardly staying on the surface of component (a). The gathered fluids are quickly brought under control by the odor-controlling agent and prevented from emitting offensive odors. Since component (a) undergoes little or no swelling, even with absorbing body fluids, the spaces in the odor-controlling member (for example, the interstices between the fibers) are not made more dense. Further, component (a) shows only a small reduction in the elastic modulus on liquid absorption so that the spaces can be stably maintained in their initial state. As a result, the body fluids do not materially remain in the spaces. Furthermore, being hydrophilic, component (a) swiftly leads the absorbed liquids to the odor-controlling agent, component (b).

The hydrophilic fiber or hydrophilic foam which does not swell with water, which is used as component (a), can be a synthetic resin which does not swell with water, such as polyethylene, polypropylene, polyester, polyurethane, and composite materials comprising two or more of these resins. Because these synthetic resins have a hydrophobic surface, they should be made hydrophilic by treatments, such as adhering a solution of a surface active agent to the synthetic resin fiber or foam by spraying or coating, or previously incorporating a hydrophilic surface active agent into the synthetic resin followed by molding the fiber or foam so that the surface active agent can bleed on the surface of the fiber or foam.

Any hydrophilic surface active agents having a lipophilic group and a hydrophilic group can be used in the above treatments. Anionic surface active agents and nonionic surface active agents having a large mole number of ethylene oxide added are preferred, such as sulfosuccinic esters, alkyl ether sulfates, polyoxyethylene alkyl ethers, polyoxyethylene alkyl phenyl ethers, and glycerol fatty acid esters. These surface active agents can be used either individually or as a mixture thereof. Still preferred among them are those capable of imparting sufficient hydrophilicity to the synthetic resins when used in amounts of about 0.05 to 3% by weight based on the resins.

The hydrophilic fiber or hydrophilic foam which does not swell with water, which is used as component (a), can also be materials that need no treatment for hydrophilicity, i.e., materials having hydrophilic surfaces in themselves. Examples of these materials include fiber or foam made of cellulose, polyvinyl alcohol and acrylic resins, such as rayon fiber, polyvinyl alcohol fiber, cellulose sponge and polyvinyl alcohol sponge.

The hydrophilic fiber or hydrophilic foam which has a centrifugal water retention of 0.7 g/g or less after equilibrium water absorption and swelling, which can be used as component (a), includes crosslinked cellulose fiber having the cellulose molecules crosslinked intramolecularly or intermolecularly with an appropriate crosslinking agent, and polynosic rayon fiber having improved crystallinity. The crosslinked cellulose fiber is preferred in consideration of economical production. Hydrophilic fiber or hydrophilic foam having a centrifugal water retention exceeding 0.7 g/g would absorb and hold body fluids and give off bad odors, or would reduce the elastic modulus on liquid absorption, allowing the liquid to remain in the interstices between the fibers or voids, which causes unpleasant odors. Chemical pulp such as softwood pulp and hardwood pulp usually has a centrifugal water retention of about 1 to 2 g/g. The method of measuring the centrifugal water retention will be described in Examples given hereinafter.

The crosslinking agent used to crosslink the cellulose preferably includes N-methylol compounds such as dimethylolethyleneurea and dimethylolhydroxyethyleneurea, polycarboxylic acids such as citric acid, tricarballylic acid, and butanetetracarboxylic acid, polyglycidyl ether compounds, and dialdehyde compounds.

The proportion of the component (a) in the odor-controlling member 9 is 20 to 80% by weight, preferably 40 to 60% by weight. If it is present in an amount of less than 20% by weight, the odor-controlling member as a whole has not only poor strength but insufficient ability to diffuse the body fluids throughout the odor-controlling agent for achieving sufficient odor-controlling effects. If the proportion is more than 80% by weight, the amount of the odor-controlling agent is too small to exhibit a high odor-controlling ability.

The term "odor-controlling agent" as used herein as component (b) is intended to mean substances in general which control the perception for bad odors, including (1) odor absorbing agents or odor decomposing agents which absorb bad odor, (2) odor preventing agents which prevent the development of bad odors, and (3) odor masking agents (aromatizers) which mask bad odors with a fragrance. The expression "controlling odor" means to control the perception of bad odors by absorbing the bad odors, preventing the development of bad odors, and masking bad odors with other odors.

Odor-controlling agents of type (2) include chelating agents containing metal ions such as silver, zinc or copper ions, and substances having these metal ions supported thereon, e.g., metal ion-impregnated zeolite.

Odor-controlling agents of type (1) include (i) those based on physical adsorption such as neutral activated carbon, fiberized carbon adsorbents, clay minerals (e.g., zeolite, amorphous silica and bentonite), active alumina and acid clay, (ii) those based on chemical decomposition such as acids, alkalis, oxidizing agents and reducing agents, (iii) physical and chemical deodorizers such as activated carbon impregnated with an acid or an alkali and zeolite impregnated with vegetable essential oil, and (iv) iron phthalocyanine derivatives, desulfurizing salts (e.g., zinc oxide), and a mixture of an iron (II) compound, L-ascorbic acid and alum.

Odor-controlling agent of type (3), i.e., aromatizers include (i) glycosides of alcoholic perfumes or glycosides comprising monosaccharides, oligosaccharides or polysaccharides, (ii) mono-, di- or triglycerides of carboxylic acid perfumes (e.g., benzoic acid and cinnamic acid), and (iii) amino acid derivatives or peptide derivatives of alcoholic perfumes, carboxylic acid perfumes or amine perfumes (e.g., indole and skatol).

The content of the odor-controlling agent in the odor-controlling member 9 is preferably 5 to 80% by weight, particularly 20 to 70% by weight. With this content, effective odor-controlling ability is exerted, the odor-controlling agent is prevented from falling off, and sufficient strength of the odor-controlling member can be secured.

The odor-controlling member 9 is composed of a layer made up of a mutually dispersing mixture of components (a) and (b) or of adjoining layers separately containing components (a) and (b). Such a layer structure is chosen according to the end use, the shape, and the like of the absorbent article. In the latter structure, either of the layer containing component (a) or the layer containing component (b) may be the upper layer. In this embodiment, the odor-controlling member 9 is an odor-controlling sheet 10 made up of a dispersing mixture of components (a) and (b), and the sheet is folded into a closed C shape.

Where the odor-controlling member 9 is formed of the odor-controlling sheet 10, the odor-controlling sheet 10 contains the hydrophilic fiber that does not swell with water or the hydrophilic fiber having a centrifugal water retention of 0.7 g/g or less (hereinafter inclusively referred to simply as hydrophilic fiber) as component (a) and the odor-controlling agent (b). In order to secure prevention of liquid from remaining in the hydrophilic fiber thereby to enhance the odor-controlling effects, it is preferred for the odor-controlling sheet 10 to contain a superabsorbent polymer. Body fluids which develop bad odors are absorbed and fixed in the superabsorbent polymer to bring about an improved odor-controlling effect. In this case, the odor-controlling sheet 10 preferably contains 20 to 80% by weight, particularly 30 to 60% by weight, of the hydrophilic fiber, 5 to 60% by weight, particularly 10 to 50% by weight, of the odor-controlling agent, and 10 to 60% by weight, particularly 20 to 50% by weight, of the superabsorbent polymer. Superabsorbent polymers conventionally employed in absorbent articles can be used.

Where the odor-controlling sheet 10 contains the superabsorbent polymer, it is desirable that the odor-controlling agent be fixedly adhered to the hydrophilic fiber via the superabsorbent polymer so that it may be prevented from falling off. Such adhesion of the odor-controlling agent can be achieved, for example, by scattering the superabsorbent polymer particles on a wet hydrophilic fiber web and then scattering the odor-controlling agent on the polymer particles that have swollen and developed stickiness.

For the purpose of increasing the strength of the odor-controlling sheet 10 or securing fixability of the odor-controlling agent to the odor-controlling sheet 10, the odor-controlling sheet 10 may contain a binder. Useful binders include heat-fusible adhesive fibers such as synthetic fibers of polyethylene, polypropylene, polyester, etc., conjugate fibers of polyethylene and polypropylene, and conjugate fibers of polyethylene and polyester; adhesive fibers which dissolve in hot water, such as polyvinyl alcohol fiber; and papermaking assistants such as carboxymethyl cellulose, Kaimen, and dialdehyde starch. The binder is preferably used in an amount of 0.1 to 30% by weight, particularly 0.5 to 10% by weight, based on the odor-controlling sheet 10.

It is desirable to improve the liquid diffusing property of the odor-controlling sheet 10 in order to exhibit the odor control function of the odor-controlling agent effectively. Specifically, it is desirable for the odor-controlling sheet 10 to have a Klemm's water absorption of 40 mm or more, particularly 50 mm or more, at 1 minute as measured for physiological saline in accordance with JIS P 8141. Such a diffusing property can be obtained by proper selection of the hydrophilic fiber. For example, in using hydrophilic fiber prepared by making synthetic fiber which does not swell with water hydrophilic, the desired diffusing property is obtained by reducing the fiber diameter to increase the specific surface area of the fiber. A preferred average fiber diameter is 20 μm or smaller, particularly 0.1 to 10 μm. The odor-controlling sheet comprising fibers with such an average diameter can be obtained conveniently, for example, by using as a base material melt-blown, nonwoven fabric that can have very fine fibers.

In using hydrophilic fiber having a centrifugal water retention of 0.7 g/g or less as component (a), it is preferred, for obtaining the desired diffusing property, to appropriately adjust the density of the odor-controlling sheet or to incorporate a small amount of very fine pulp fibers having a large specific surface area, e.g., hardwood pulp fibers, into the odor-controlling sheet.

While the absorbent member 4 according to the embodiment of FIG. 1 is totally formed of the odor-controlling member 9, modifications can be made in such a manner that the odor-controlling member constitutes a part of the absorbent member and is disposed in any portion of the absorbent member. In this case, the other part of the absorbent member can be made of fluff pulp, a superabsorbent polymer, absorbent paper, and the like. In order for the absorbent member 4 to perform a sufficient odor-controlling function while maintaining desired absorbing performance, it is preferred for the absorbent member 4 to comprise component (a) in a proportion of 5 to 70% by weight, particularly 10 to 60% by weight, and component (a) in a proportion of 5 to 70% by weight, particularly 10 to 50% by weight of the total weight of the absorbent member 4. To obtain sufficient odor-controlling performance, the weight proportion of the odor-controlling member in the total absorbent member 4 is preferably 10% by weight or more, particularly 20% by weight or more.

The position where the odor-controlling member is to be disposed is not particularly limited. It is preferred for effective prevention of bad odor development from the absorbed body fluids that the odor-controlling member be placed in the uppermost portion of the absorbent member, i.e., on the side of the surface to be in contact with the wearer's skin. Where the odor-controlling member is arranged in the uppermost portion of the absorbent member, it is preferred for the odor-controlling member to occupy at least 50%, particularly 70 to 100%, of the total area of the skin-contacting surface side of the absorbent member.

Where the backsheet as a leakproof layer is permeable to steam, an increase in humidity in the absorbent article while worn can be suppressed by breathing, to give a wearer comfort without stuffiness. Such breathability controls growth of bacteria, which contributes to suppression of the progress of liquid decomposition and prevention of the development and increase of bad odors. In this case, however, there is the fear that the steam-permeable backsheet may permit the bad odors of the absorbed body fluids to escape to the outside out of the absorbent article. It is therefore desirable that the odor-controlling member of the absorbent layer be disposed in contact with the leakproof layer when it is steam-permeable.

Figure 2:
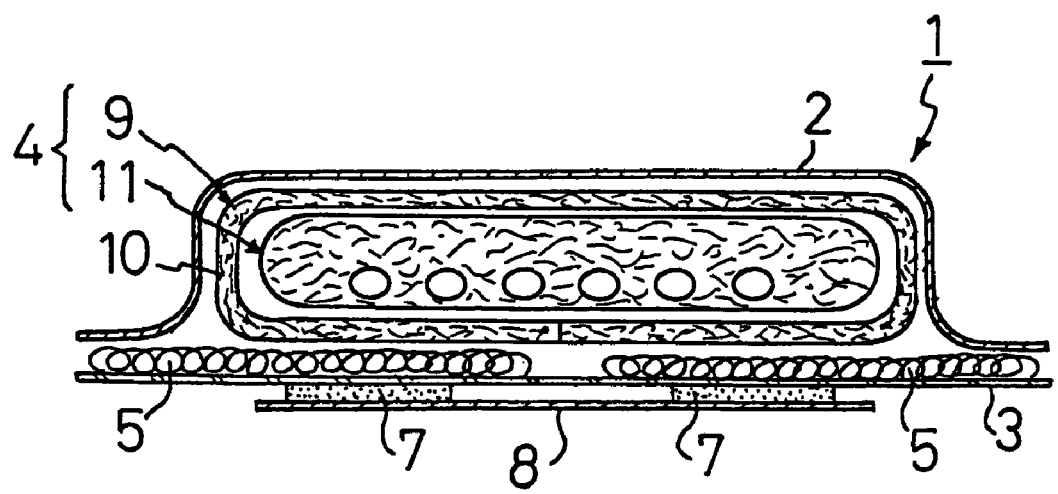
FIG. 2 is a cross-sectional view in the width direction of a sanitary napkin, showing another embodiment of the absorbent article according to the present invention.

In FIG. 2 is shown a sanitary napkin as another embodiment of the absorbent article of the present invention in which an odor-controlling member is arranged in the uppermost portion of the absorbent layer and also in contact with the leakproof layer. Specifically, the absorbent member 4 is composed of an absorbent and retentive member 11 made up of a dispersing mixture of fluff pulp and a superabsorbent polymer and an odor-controlling member 9 that is an odor-controlling sheet 10 covering the upper and lower surfaces and both lateral sides of the absorbent and retentive member 11. The absorbent member 4 is interposed between the topsheet 2 and the steam-permeable backsheet 3, the absorbent member 4 and the backsheet 3 being fixed to each other via a spirally applied hot-melt adhesive 5 disposed on the lower surface side of the absorbent member 4. The topsheet 2 and the backsheet 3 extend from the lateral edges of the absorbent member 4 and are bonded together with a hot-melt adhesive 5. The sanitary napkin 1 according to this embodiment effectively prevents development of unpleasant odors from the absorbed body fluids similar to the first embodiment.

The present inventors have analyzed the gas emitted from soiled sanitary napkins and panty liners after actual use when stored in a closed glass container (hereinafter described) for 30 minutes under the conditions hereinafter described and found that a variety of offensive odors develop; that is, ammonia reaching ten-odd ppm at the most, mercaptans reaching several tens of ppm at the most, amines reaching a hundred and several tens of ppm at the most, fatty acids reaching ten-odd ppm at the most, and ketones and others reaching several tens of ppm at the most.

As a result of further investigations, the inventors have ascertained that odor-controlling ability in a dry state (hereinafter referred to as dry odor-controlling ability), odor-controlling ability in a wet state (hereinafter referred to as wet odor-controlling ability), and odor-controlling ability in a dry/wet combined state (hereinafter referred to as combined odor-controlling ability) are important attributes required of absorbent articles and that absorbent articles which clear specific levels of these attributes of odor-controlling ability would satisfy users.

That is, the absorbent article according to the present invention has the following dry odor-controlling ability before absorbing body fluids. A 29% by weight of an aqueous ammonia (available from Kanto Chemical Co., Ltd.) precisely measuring 0.1 µL is put into a 900 mL glass container by means of a microsyringe, and immediately thereafter a test absorbent article is put in the glass container. The glass container is closed tightly and kept at 25° C. for 30 minutes to 3 hours. The satisfactory dry odor-controlling ability is such that the ammonia gas concentration in the glass container after 30 minute storage is less than 10 ppm, preferably 5 ppm or less, and that that concentration after 3 hour storage is 5 ppm or less, preferably 3 ppm or less. Further, methyl mercaptan for odor measurement (a 1 µg/µL benzene solution; available from Wako Pure Chemical Industries, Ltd.) precisely measuring 100 µL is put into a 900 mL glass container by means of a microsyringe, and immediately thereafter a test absorbent article is put in the glass container. The glass container is tightly closed and kept at 25° C. for 30 minutes to 3 hours. The satisfactory dry odor-controlling ability is such that the methyl mercaptan gas concentration in the glass container after 30 minute storage is 20 ppm or less, preferably 10 ppm or less, and that that concentration after 3 hour storage is 2 ppm or less, preferably 1 ppm or less.

The above-defined dry odor-controlling ability is the most fundamental attribute concerning odor control of the absorbent article of the present invention. This is the ability to control bad odors while the absorbent article is being worn but is substantially free from body fluids. The bad odors to be controlled in this case include those from the body fluids that have already existed on the skin or those of gas from the body. Both ammonia gas and methyl mercaptan gas are components of bad odors originated in discharged body fluids. An ammonia gas concentration of 10 ppm or higher may be perceived as a bad odor by a wearer, and an ammonia gas concentration of several tens of ppm or higher might be perceived as a bad odor by others. A methyl mercaptan gas concentration of several to about 10 ppm may be perceived as a bad odor by a wearer, and the concentration of 20 ppm or higher might be perceived by others. Because the absorbent article of the present invention satisfies the above-specified dry odor-controlling ability, i.e., ammonia gas and methyl mercaptan gas concentration after 30 minute storage and 3 hour storage, it reduces the bad odors generated from the discharged body fluids to the imperceptible level at minimum quickly after being put on a wearer (within 30 minutes) and achieves odor control almost completely in an average wearing time of a sanitary napkin (usually 2 to 3 hours).

The above-described dry odor-controlling ability is measured as follows. Prescribed amounts of test liquids are introduced into tightly sealable 900 mL glass containers respectively by means of a microsyringe, and immediately thereafter absorbent articles are put in the containers, respectively, and the containers are tightly closed. The test liquid is introduced in the form of an aqueous solution or a solution in other solvents. In the present invention, ammonia gas is introduced as 29% by weight of an aqueous solution, and methyl mercaptan gas is introduced as a 1 µg/µL benzene solution. The initial ammonia gas concentration and the initial methyl mercaptan gas concentration in the glass container are about 200 ppm and about 80 ppm, respectively. After 30 minutes from the closure, each container is opened a crack so that the inside gas may not escape, and the ammonia and methyl mercaptan gas concentrations are measured with respective detectors supplied by Gastec Service, Inc. (No. 3L or No. 3La for ammonia gas detection and No. 70 or No. 70L for methyl mercaptan gas detection, chosen according to concentrations). The gas concentrations after 3 hours are measured on separate testing systems prepared in the same manner. That is, the gas concentrations after 30 minutes and those after 3 hours are not measured with the same glass containers. Any glass container having a capacity of 900 mL is usable as far as it is tightly sealable and free from any odor. For the convenience of putting a test absorbent article and for sucking the gas, a wide-mouthed bottle is preferred. Laboratory wear, such as a UM sucking bottom (900 mL), and general-purpose bottles, such as a mayonnaise bottle (900 mL) supplied by Toyo Glass K.K. (used in the present invention), are suitable. The environment of working such as putting the absorbent article and the test liquids into the glass container is 25° C. and 45-65 RH (this environment is the same as that in the wet odor-controlling ability and the combined odor-controlling ability).

The gas concentrations are measured under the following conditions.

(1) Suction Apparatus
   GV-100S manufactured by Gastec Service, Inc. was used in common to ammonia gas and methyl mercaptan gas. A 100 mL gas portion is sucked per operation. The suction time is 1 minute as instructed.

(2) Ammonia Concentration
   Detector No. 3La (available from Gastec Service, Inc.) is used for high concentrations (30 ppm or higher), and Detector No. 3L (available from Gastec Service, Inc.) for low concentrations (less than 30 ppm). The ammonia concentration is obtained from the range of the detector's color-change.

(3) Methyl Mercaptan Concentration
   Detector No. 70 (available from Gastec Service, Inc.) is used for high concentrations (5 ppm or higher), and Detector No. 70L (available from Gastec Service, Inc.) for low concentrations (4 ppm or lower). The methyl mercaptan concentration is obtained from the range of the detector's color change.

When the color change stops in the middle of scale marks, the concentration is calculated proportionally using the upper and lower scale marks. Measurement is made three times using triplicate samples to obtain an average value. Since 100 mL of the gas in the container is consumed by suction for each measurement, repetition of measurement on the same sample that causes errors is avoided. Therefore, the measurement after 30 minutes and that after 3 hours are made on separately prepared samples.

Further, the absorbent article according to the present invention preferably has the following wet odor-controlling ability, which is the odor-controlling performance in a state wetted with liquid. 60 µL of 29% by weight of an aqueous ammonia and 5 mL of physiological saline are applied in this order to the same portion of a test absorbent article, and immediately thereafter the absorbent article is put in a 900 mL glass container. The glass container is tightly closed right away and kept at 25° C. for 30 minutes to 3 hours. The preferred wet odor-controlling ability is such that the ammonia gas concentration in the glass container after 30 minute storage is 20 ppm or less, particularly 15 ppm or less, and that that concentration after 3 hour storage is 7 ppm or less, particularly 5 ppm or less.

Further, when 100 µL of a 1 µg/µL benzene solution of methyl mercaptan and 5 mL of physiological saline are applied in this order to the same portion of a test absorbent article, and the article is stored in the same manner as described above, the preferred wet odor-controlling ability is such that the methyl mercaptan gas concentration in the glass container after 30 minute storage is 10 ppm or less, particularly 5 ppm or less, and that that concentration after 3 hour storage is 2 ppm or less, particularly 1 ppm or less.

The above-defined wet odor-controlling ability indicates the ability of the absorbent article of the present invention to control odors even in a wet state after liquid absorption, i.e., the ability to shut up the odors emitted from absorbed body fluids. A huge majority of bad odors are given off from components dissolved in body fluids such as menstrual blood and discharged out of the body. Therefore, after body fluids are once absorbed in the absorbent article, to make sure that the bad odors are trapped not to be released from the absorbent article will secure extremely high odor-controlling effects. This ability is the above-defined wet odor-controlling ability. While conditions required for the wet odor control are basically the same as those for the dry odor control, the change in odor concentrations differ. At least the odor concentrations in a short time (30 minutes) are more meaningful for wet odor control than for dry odor control. In more detail, in the measurement of dry odor-controlling ability, the odor concentration decreases monotonously from the very beginning. In the measurement of wet odor-controlling ability, on the other hand, the odor concentration increases steeply for a while immediately after introducing the liquid into the glass container and tightly closing it because the odor dissipates from the absorbent article and, after reaching the peak, it decreases. In 30 minutes, the decrease in odor concentration becomes monotonous. Accordingly, with the peak of the odor concentration appearing between 0 and 30 minutes, the odor might be perceived by the people around the wearer unless the peak concentration is reduced enough.

The peak concentration varies largely depending on the properties or distribution of the body fluids so that it is difficult to specify the wet odor-controlling ability with reference to the peak concentration. On the other hand, an absorbent article that shows an ability to sufficiently reduce the odor concentration in 30 minutes (by that time the decrease in odor concentration has become monotonous) may not render the peak concentration extremely high and is therefore deemed to have effective wet odor-controlling ability. This is the reason why the odor concentration after 30 minutes is used as a measure of the wet odor-controlling ability. Where the absorbent article of the present invention satisfies the above-specified wet odor-controlling ability in terms of the ammonia gas and methyl mercaptan gas concentrations after 30 minute storage, the concentrations of bad odors dissipated from the discharged body fluids are prevented from increasing steeply and kept below the perceptible levels. Further, where the absorbent article satisfies the above-specified wet odor-controlling ability after 3 hour storage, the odors are under control almost perfectly in an average wearing time of a sanitary napkin (usually 2 to 3 hours).

The above-described wet odor-controlling ability is measured as follows. Prescribed amounts of the above-mentioned test liquids are poured into the central portion of absorbent articles, respectively, and immediately thereafter the absorbent articles are put in tightly sealable 900 mL glass containers, respectively, and the containers are tightly closed. The aqueous ammonia and the methyl mercaptan solution are poured with microsyringes, and physiological saline is poured with a measuring pipette or a transfer pipette. Measurement of the gas concentrations is carried out in the same manner as for the dry odor-controlling ability.

Furthermore, the absorbent article according to the present invention preferably has the following combined odor-controlling ability, which is the performance of controlling bad odors developed from the absorbed body liquids and from the body after absorption of body fluids. 0.1 µL of 29% by weight of an aqueous ammonia is put into a 900 mL glass container, and immediately thereafter an absorbent article having absorbed 60 µL of 29% by weight of an aqueous ammonia and 5 mL of physiological saline in this order is put in the glass container. The glass container is closed right away and kept at 25° C. for 30 minutes to 3 hours. The preferred combined odor-controlling ability is such that the ammonia gas concentration in the glass container after 30 minute storage is 20 ppm or less, particularly 15 ppm or less, especially 10 ppm or less, and that that concentration after 3 hour storage is 7 ppm or less, particularly 5 ppm or less, especially 2 ppm or less.

When 100 µL of a 1 µg/µL benzene solution of methyl mercaptan is introduced into a 900 mL glass container, and immediately thereafter an absorbent article having adsorbed 100 µL of a 1 µg/µL benzene solution of methyl mercaptan and 5 mL of physiological saline in this order is put into the container and stored in the same manner as described above, the preferred combined odor-controlling ability is such that the methyl mercaptan gas concentration in the glass container after 30 minute storage is 20 ppm or less, particularly 10 ppm or less, especially 5 ppm or less, and that that concentration after 3 hour storage is 2 ppm or less, particularly 1 ppm or less.

The above-defined combined odor-controlling ability is an effective indication in evaluating the overall ability to control bad odors of the absorbent article in actual use. Absorbent articles are to undergo reduction of odor-controlling performance in actual use because, for one thing, the odor-controlling agent is wetted by body fluids and, for another, the odor-controlling agent reduces its effect while being repeatedly used for controlling bad odors (in particular, an order-adsorbing agent loses its adsorptivity due to saturation).

The combined odor-controlling ability is the ability to control bad orders even after adsorbing body fluids. Where the absorbent article of the present invention satisfies the above-specified combined odor-controlling ability in terms of the ammonia gas and methyl mercaptan gas concentrations after 30 minute storage, the concentrations of bad odors dissipated from the discharged body fluids can be controlled below perceptible levels rapidly (in 30 minutes). In particular, where the concentrations of the ammonia gas and the methyl mercaptan gas in 30 minute storage are reduced to 20 ppm or less each, there would appear no peak concentration ascribed to re-release of gases from the inside of the absorbent article, thus a fear of the bad odors' being perceived will be further lessened. Where the absorbent article satisfies the above-specified combined odor-controlling ability after 3 hour storage, the odors are under control almost perfectly in an average wearing time of a sanitary napkin (usually 2 to 3 hours).

The combined odor-controlling ability can be measured as follows. In sealable 900 mL glass containers are introduced 0.1 µL of 29% by weight of an aqueous ammonia and 100 µL of a 1 µg/µL benzene solution of methyl mercaptan, respectively, in the same manner as in the measurement of dry odor-controlling ability. Immediately thereafter, absorbent articles, which are prepared in the same manner as in the measurement of wet odor-controlling ability, the one having absorbed in the central portion thereof 60 µL of 29% by weight of an aqueous ammonia and 5 mL of physiological saline in this order, and the other having absorbed in the central portion thereof 100 µL of a 1 µg/µL benzene solution of methyl mercaptan and 5 mL of physiological saline in this order are put into the glass containers, respectively, and the containers are sealed and stored. The absorbent articles are put into the glass containers immediately after absorbing these liquids. The gas concentration in the glass containers is measured in the same manner as for dry odor-controlling ability.

The absorbent article of the present invention exhibits satisfactory dry, wet, and combined odor-controlling abilities against not only ammonia and mercaptans but other unpleasant odors given out from menstrual blood or discharge.

Specifically, the absorbent article preferably has the following dry odor-controlling ability (at 25° C.) against diethylamine and acetic acid. In the evaluation, the amount of diethylamine introduced into a glass container is 0.2 µL, and the amount of acetic acid introduced into a glass container is 0.08 µL.

| Diethylamine gas concentration: | |
| --- | --- |
| After 30 minutes: | 20 ppm or less, particularly 10 ppm or less |
| After 3 hours: | 10 ppm or less, particularly 5 ppm or less |
| Acetic acid gas concentration: | |
| After 30 minutes: | 10 ppm or less, particularly 7 ppm or less |
| After 3 hours: | 10 ppm or less, particularly 5 ppm or less |

The absorbent article preferably has the following wet odor-controlling ability (at 25° C.) against diethylamine and acetic acid. In the evaluation, 100 µL of diethylamine is poured on an absorbent article with a microsyringe, and then 5 mL of physiological saline is poured with a measuring pipette or a transfer pipette. 80 µL of acetic acid is poured on an absorbent article with a microsyringe, and then 5 mL of physiological saline is poured with a measuring pipette or a transfer pipette.

| Diethylamine gas concentration: | |
| --- | --- |
| After 30 minutes: | 20 ppm or less, particularly 10 ppm or less |
| After 3 hours: | 10 ppm or less, particularly 5 ppm or less |
| Acetic acid gas concentration: | |
| After 30 minutes: | 10 ppm or less, particularly 7 ppm or less |
| After 3 hours: | 10 ppm or less, particularly 5 ppm or less |

The absorbent article preferably has the following combined odor-controlling ability (at 25° C.) against diethylamine and acetic acid. In the evaluation, diethylamine and acetic acid are introduced into glass containers, respectively, in the same manner as in the measurement of dry odor-controlling ability, and an absorbent article is wetted in the same manner as in the measurement of wet odor-controlling ability.

| Diethylamine gas concentration: | |
| --- | --- |
| After 30 minutes: | 40 ppm or less, particularly 20 ppm or less |
| After 3 hours: | 10 ppm or less, particularly 7 ppm or less |
| Acetic acid gas concentration: | |
| After 30 minutes: | 20 ppm or less, particularly 15 ppm or less |
| After 3 hours: | 10 ppm or less, particularly 5 ppm or less |

In the measurement of dry, wet, and combined odor-controlling abilities against diethylamine and acetic acid, diathylamine concentration was measured by GV-100S manufactured by Gastec Service, Inc. Detector No. 180L was used for measurement of diethylamine concentrations less than 10 ppm, and Detector No. 180 for diethylamine concentrations between 10 and 100 ppm, in accordance with the instructions. Detector No. 180 was used for concentrations higher than that while changing the amount of suction. Detector No. 81L was used for acetic acid concentrations less than 10 ppm, and Detector No. 81 for acetic acid concentrations higher than that, in accordance with the instructions. All these detector models are available from Gastec.

In regard to odor-controlling performance, especially wet and combined odor-controlling abilities, conventional absorbent articles fail to sufficiently shut up bad odors developing from absorbed body fluids and to produce sufficient odor-controlling effects. To the contrary, the absorbent article according to the present invention which has the above-described odor-controlling member exhibits an excellent effect in keeping the bad orders confined and, based on such an effect, exhibits superior odor-controlling effects on various bad odors at various temperatures, especially at relatively high temperatures around a body temperature.

The conventional absorbent articles have overlooked the influences of temperature (body temperature) upon odor-controlling performance. When an absorbent article is warmed by a body temperature, a heavier load is imposed on the absorbent article and the odor-controlling agent than at a room temperature so that the gas adsorbing ability of the odor-controlling agent relatively reduces, and gas is diffused more easily. Specifically, the following phenomena occur in an absorbent article that is warmed by a body temperature and is wetted with body fluids.

1) Reduction in function of the odor-controlling agent.
2) Increase in amount of bad odors developing from the discharged body fluids.
3) Increase in amount of bad odors with progress of decomposition of the discharged body fluids.

However, the absorbent article of the present invention manifests sufficient odor-controlling effects even in temperatures around a body temperature.

Specifically describing, the absorbent article of the present invention preferably shows the following dry odor-controlling ability when stored and measured at 40° C.:

Ammonia gas concentration:

| | |
|---|---|
| After 30 minutes: | 15 ppm or less, particularly 10 ppm or less, especially 5 ppm or less |
| After 3 hours: | 7 ppm or less, particularly 5 ppm or less, especially 3 ppm or less |

Methyl mercaptan gas concentration:

| | |
|---|---|
| After 30 minutes: | 20 ppm or less, particularly 10 ppm or less, especially 5 ppm or less |
| After 3 hours: | 5 ppm or less, particularly 2 ppm or less |

Amine gas concentration:

| | |
|---|---|
| After 30 minutes: | 20 ppm or less, particularly 15 ppm or less, especially 10 ppm or less |
| After 3 hours: | 5 ppm or less, particularly 3 ppm or less |

Acetic acid gas concentration:

| | |
|---|---|
| After 30 minutes: | 15 ppm or less, particularly 10 ppm or less, especially 7 ppm or less |
| After 3 hours: | 10 ppm or less, particularly 7 ppm or less. |

The absorbent article of the present invention preferably has the following wet odor-controlling ability when stored at 40° C.:

Ammonia gas concentration:

| | |
|---|---|
| After 30 minutes: | 50 ppm or less, particularly 30 ppm or less, especially 20 ppm or less |
| After 3 hours: | 30 ppm or less, particularly 20 ppm or less |

Methyl mercaptan gas concentration:

| | |
|---|---|
| After 30 minutes: | 20 ppm or less, particularly 15 ppm or less, especially 10 ppm or less |
| After 3 hours: | 20 ppm or less, particularly 10 ppm or less |

Amine gas concentration:

| | |
|---|---|
| After 30 minutes: | 50 ppm or less, particularly 40 ppm or less, especially 30 ppm or less |
| After 3 hours: | 30 ppm or less, particularly 20 ppm or less |

Acetic acid gas concentration:

| | |
|---|---|
| After 30 minutes: | 30 ppm or less, particularly 25 ppm or less, especially 20 ppm or less |
| After 3 hours: | 10 ppm or less, particularly 7 ppm or less. |

The absorbent article of the present invention preferably has the following combined odor-controlling ability when stored at 40° C.:

Ammonia gas concentration:

| | |
|---|---|
| After 30 minutes: | 60 ppm or less, particularly 50 ppm or less, especially 40 ppm or less |
| After 3 hours: | 20 ppm or less, particularly 15 ppm or less |

Methyl mercaptan gas concentration:

| | |
|---|---|
| After 30 minutes: | 70 ppm or less, particularly 60 ppm or less, especially 50 ppm or less |
| After 3 hours: | 70 ppm or less, particularly 60 ppm or less |

Amine gas concentration:

| | |
|---|---|
| After 30 minutes: | 70 ppm or less, particularly 60 ppm or less, especially 50 ppm or less |
| After 3 hours: | 30 ppm or less, particularly 20 ppm or less |

Acetic acid gas concentration:

| | |
|---|---|
| After 30 minutes: | 30 ppm or less, particularly 25 ppm or less, especially 20 ppm or less |
| After 3 hours: | 20 ppm or less, particularly 10 ppm or less. |

Since the absorbent article of the present invention has the odor-controlling member in the absorbent member thereof, the odor-controlling member comprising an odor-controlling agent and specific hydrophilic fiber or hydrophilic foam in a specific ratio, absorbed body fluids hardly stay in the spaces in the odor-controlling member so that development of bad odors in the spaces can be prevented. Further, the absorbed liquid migrates to the odor-controlling agent and is thereby under odor control. Where a superabsorbent polymer is used in combination in the odor-controlling member, because the liquid is absorbed and fixed by the superabsorbent polymer, odor control can be achieved more efficiently. Thus, the present invention makes it feasible to provide an absorbent article which is capable of controlling unpleasant odors developing from absorbed liquid below perceptible levels or bothering levels.

Since the absorbent article of the present invention exhibits odor-controlling performance against specific gases under specific conditions, it has high odor-controlling effects to keep bad odors developing from absorbed body liquids below perceptible levels or bothering levels. Further, since the absorbent article of the present invention possesses both quick odor-controlling ability (after a lapse of 30 minutes) against specific gases and long-lasting odor-controlling ability (after a lapse of 3 hours), it has high odor-controlling effects during use, and its odor is not bothering when it is removed or exchanged. Excellent in odor-controlling performance against specific gases corresponding to the menstrual odors, the absorbent article of the present invention is especially useful as a sanitary napkin.

The present invention is not restricted by the aforementioned embodiments. For example, the absorbent member 4 in the napkin 1 shown in FIG. 1 can be replaced with the absorbent member used in the napkin shown in FIG. 2, or vice versa. The absorbent article of the present invention is applicable to not only sanitary napkins but disposable diapers, incontinence pads, panty liners, underlaying sheets for keeping pets and the like.

The present invention will now be illustrated in greater detail with reference to Examples. The following Examples are presented as being exemplary of the present invention and should not be considered as limiting. Unless otherwise noted, all the parts and percents are by weight.

EXAMPLES

Preparation of Odor-Controlling Sheet A

Ninety-five parts of crosslinked pulp having a centrifugal water retention of 0.3 g/g (tradename: HBA, supplied by Weyerhauser Paper Co.) and 5 parts of polyvinyl alcohol fiber (binder) having a thickness of 1 denier and a fiber length of 3 mm (tradename: Fibribond, supplied by Sansho K.K.) were dispersed and mixed in water to prepare a papermaking slurry having a prescribed concentration. The slurry was fed to the papermaking part of a wet papermaking machine and made into a web having a dry basis weight of 30 g/m² which was to be used as a lower layer fibrous sheet. The lower layer fibrous sheet was dehydrated in the suction box to reduce the water content to 60%, and a superabsorbent polymer (tradename: Aquaric, available from Nippon Shokubai Kagaku Kogyo Co., Ltd.) was scattered thereon almost uniformly to give a basis weight of 30 g/m². Then granular activated carbon (CW480B, available from Futamura Kagaku K.K.) as an odor-controlling agent was scattered thereon almost uniformly to give a basis weight of 30 g/m². An absorbent sheet having a basis weight of 40 g/m² which had previously been prepared from the same composition as the lower layer fibrous sheet was superposed on the superabsorbent polymer and activated carbon. The laminated web was made into one body by drying at 130° C. in a Yankee drier to obtain an odor-controlling sheet A having in the inside thereof the superabsorbent polymer and activated carbon embedded in a dispersingly mixed state. It was confirmed that the activated carbon granules were fixedly adhered to the crosslinked pulp via the superabsorbent polymer particles.

Preparation of Odor-Controlling Sheet B:

An odor-controlling sheet B was prepared in the same manner as in the preparation of the odor-controlling sheet A, except that granular activated carbon (CW480B, available from Futamura Kagaku K.K.) and bentonite (tradename: Benclay, available from Mizusawa Kagaku K.K.) were scattered as odor-controlling agents in amounts of 30 g/m² and 20 g/m², respectively. In the resulting odor-controlling sheet B, the activated carbon and bentonite were found fixedly adhered to the crosslinked pulp via the superabsorbent polymer particles.

Preparation of Odor-Controlling Sheet C:

An ethylene-1-octene copolymer resin (density: 0.93 g/cc) was mixed with 1%, based on the resin, of a mixed (1:1) surface active agent of glycerol monostearate and polyoxyethylene nonyl phenyl ether (tradename: Emulgen 935, available from Kao Corp.; number of moles of ethylene oxide added: 35). The resin was fabricated into a web by melt blowing to obtain a melt-blown nonwoven fabric having been made hydrophilic and having a basis weight of 40 g/m². The resin constituting the nonwoven fabric was non-swellable with water and had an average fiber diameter of about 1 μm. A superabsorbent polymer (tradename: Aquaric, available from Nippon Shokubai Kagaku Kogyo Co., Ltd.) was scattered on the nonwoven fabric to give a basis weight of 30 g/m². A slight amount of water was sprayed thereon to swell the superabsorbent polymer, and granular activated carbon (CW480B, available from Futamura Kagaku K.K.) as an odor-controlling agent was scattered thereon almost uniformly to give a basis weight of 30 g/m². The same meltblown hydrophilic nonwoven fabric (basis weight: 40 g/m²) as used above was put thereon and dried to obtain unitary odor-controlling sheet C. In the odor-controlling sheet C the activated carbon was fixedly adhered to the resin fibers via the superabsorbent polymer particles.

Preparation of Odor-Controlling D:

A melt brown hydrophilic nonwoven fabric (basis weight: 40 g/m²) was obtained in the same manner as in the preparation of the odor-controlling sheet C. Granular activated carbon (CW480B, available from Futamura Kagaku K.K.) and bentonite (tradename: Benclay, available from Mizusawa Kagaku K.K.) as odor-controlling agents were scattered thereon almost uniformly to give basis weights of 30 g/m² and 30 g/m², respectively. Afterward, the same preparation manner as in the odor-controlling sheet C was repeated to obtain an odor-controlling sheet D.

Preparation of Odor-Controlling Sheet E (Comparison):

Softwood chemical pulp having a centrifugal water retention of 1.3 g/g (tradename: Skeena Prime, available from Skeena Cellulose Co.) was dispersed in water, and the slurry was fabricated into absorbent paper having a basis weight of 40 g/m². A hot-melt adhesive was applied in a spiral to the absorbent paper in an amount of 10 g/m², and 30 g/m² of granular activated carbon (CW480B, available from Futamura Kagaku K.K.) and 30 g/m² of bentonite (tradename: Benclay, available from Mizusawa Kagaku K.K.) as odor-controlling agents were scattered thereon almost uniformly. The same absorbent paper (basis weight: 40 g/m²) as prepared above was laid thereon to obtain a unitary odor-controlling sheet E.

Preparation of Odor-Controlling Sheet F (Comparison):

Chemical pulp (tradename: NB-420, supplied by Weyerhauser Paper Co.) having a centrifugal water retention of 1.2 g/g was air-laid to form a web having a basis weight of 50 g/m², and 30 g/m² of a superabsorbent polymer (tradename: Aquaric, available from Nippon Shokubai Kagaku Kogyo Co., Ltd.) and 30 g/m² of granular activated carbon (CW480B, available from Futamura Kagaku K.K.) as odor-controlling agents were scattered thereon almost uniformly. The same chemical pulp as used above was air-laid thereon to give a basis weight of 50 g/m², and the laminate was compressed into a unitary odor-controlling sheet F.

Preparation of Absorbent Sheet G (Comparison):

Softwood chemical pulp having a centrifugal water retention of 1.3 g/g (tradename: Skeena Prime, available from Skeena Cellulose Co.) was dispersed in water, and the slurry was made into an absorbent sheet G having a basis weight of 40 g/m².

The centrifugal water retention of the fibers constituting the above prepared odor-controlling sheets A to F and the absorbent sheet G and the Klemm's water absorption of these sheets were measured in accordance with the following methods. The results obtained are shown in Table 1.

1) Centrifugal Water Retention

A hydrophilic material sample, such as fiber or foam, precisely weighing 1 g was put in a beaker containing 500 mL of ion-exchanged water and left to stand for 30 minutes. The sample was taken out of water and put into a bag made of nonwoven cloth or nylon mesh that would not let the sample fall out. The bag was centrifuged on a centrifuge (tradename: H-130C, manufactured by Kokusan Enshinki K.K.) at 2000 rpm (centrifugal acceleration: 895 G) for 10 minutes. The sample was weighed to obtain a water retention after centrifugation (centrifugal water retention) according to the following equation:

Centrifugal water retention(g/g)=[weight of sample after centrifugation initial weight of sample(1 g)]/initial weight of sample(1 g)

2) Klemm's Water Absorption

A Klemm's water absorption of the odor-controlling sheets A to F and the absorbent sheet G was measured in accordance with the conditions and apparatus specified in JIS P 8141, except for using physiological saline as a test liquid. The sample was 15 mm wide and 200 mm long, the length corresponding to the longitudinal direction of absorbent articles. After 1 minute dipping in physiological saline, the height of water absorption from the liquid level was measured. Measurement was repeated 10 times to obtain an average value in one minute.

TABLE 1

| Odor-Controlling Sheet | Total Basis Weight (g/m²) | Hydrophilic Fiber Centrifugal Water Retention (g/g) | Material | Ratio in Sheet (wt %) | Odor-Controlling Agent Material | Amount (g/m²) | Ratio in Sheet (wt %) | Super-absorbent Polymer (g/m²) | Klemm's Water Absorption (mm) |
|---|---|---|---|---|---|---|---|---|---|
| A | 130 | 0.3 | crosslinked pulp | 51 | activated carbon | 30 | 23 | 30 | 55 |
| B | 150 | 0.3 | crosslinked pulp | 44 | activated carbon | 30 | 33 | 30 | 53 |
|   |   |   |   |   | bentonite | 20 |   |   |   |
| C | 140 | water non-swellable | polyethylene (made hydrophilic) | 57 | activated carbon | 30 | 21 | 30 | 60 |
| D | 140 | water non-swellable | polyethylene (made hydrophilic) | 57 | activated carbon | 30 | 43 | — | 57 |
|   |   |   |   |   | bentonite | 30 |   |   |   |
| E | 150 | 1.3 | chemical pulp | 53 | activated carbon | 30 | 40 | — | 25 |
|   |   |   |   |   | bentonite | 30 |   |   |   |
| F | 160 | 1.2 | chemical pulp | 63 | activated carbon | 30 | 19 | 30 | 33 |
| absorbent sheet G | 40 | 1.3 | chemical pulp | 100 | none | — | — | — | 31 |

Example 1

A sanitary napkin shown in FIG. 1 was prepared. The odor-controlling sheet A of 150 mm in width and 175 mm in length was folded into a closed C shape to make an absorbent member 4. The absorbent member 4 was wrapped in a 100 mm wide and 205 mm long leakproof sheet 6 of polyethylene film and further wrapped in a 120 mm wide and 205 mm long liquid-permeable topsheet 2 of perforated polyethylene film. A backsheet 3 of polyethylene film was laid over the absorbent member 4 thus wrapped and fixed at the longitudinal ends by heat sealing. A hot-melt adhesive 7 was applied to the side of skin non-contacting surface of the napkin for fixing to a wearer's undergarment, and a release sheet 8 was put thereon. The resulting sanitary napkin was 75 mm in width and 205 mm in length.

Example 2

A sanitary napkin was made in the same manner as in Example 1, except for replacing the odor-controlling sheet A with the odor-controlling sheet B.

Example 3

Chemical pulp (tradename: NB-420 supplied by Weyerhauser Paper Co.) was air-laid to obtain a web having a basis weight of 150 g/m², a width of 70 mm and a length of 175 mm. A superabsorbent polymer (tradename: Aquaric, available from Nippon Shokubai Kagaku Kogyo Co., Ltd.) was scattered on the web in an amount of 30 g/m². The superabsorbent polymer/pulp web was wrapped in the 150 mm wide and 175 mm long odor-controlling sheet C to make an absorbent member. A sanitary napkin was prepared by using the resulting absorbent member in the same manner as in Example 1.

Example 4

A sanitary napkin was obtained in the same manner as in Example 3, except for replacing the odor-controlling sheet C with the odor-controlling sheet D.

Comparative Example 1

Chemical pulp (tradename: NB-420, supplied by Weyerhauser Paper Co.) was air-laid to make a 70 mm wide and 175 mm long web having a basis weight of 150 g/m². A superabsorbent polymer (tradename: Aquaric, available from Nippon Shokubai Kagaku Kogyo Co., Ltd.) was scattered on the web in an amount of 30 g/m². The odor-controlling sheet E of 70 mm in width and 175 mm in length was placed under the superabsorbent polymer/pulp web, and the whole laminate was wrapped in 115 mm wide and 175 mm long wet absorbent paper having a basis weight of 18 g/m², the wet absorbent paper being made of softwood chemical pulp having a centrifugal water retention of 1.3 g/g (tradename: Skeena Prima, available from Skeena Cellulose Co.), to make an absorbent member. A sanitary napkin was prepared by using the resulting absorbent member in the same manner as in Example 1.

Comparative Example 2

A sanitary napkin was obtained in the same manner as in Comparative Example 1, except for replacing the odor-controlling sheet E with the odor-controlling sheet F.

Comparative Example 3

A commercially available sanitary napkin, "tradename: LAURIER, SOFT MESH Regular" supplied by Kao Corp., was used as Comparative Example 3.

Examples 5 and 6 and Comparative Example 4 hereinafter given show examples in which a moisture permeable leakproof material was used in the leakproof layer for further improving the stuffiness and enhancing user's comfort.

Example 5

A sanitary napkin shown in FIG. 2 was prepared. Chemical pulp (tradename: NB-420, supplied by Weyerhauser Paper Co.) was air-laid to make a 70 mm wide and 175 mm long web having a basis weight of 150 g/m$^2$. A superabsorbent polymer (tradename: Aquaric, available from Nippon Shokubai Kagaku Kogyo Co., Ltd.) was scattered on the web to give a basis weight of 30 g/m$^2$. The superabsorbent polymer/pulp web was wrapped in the 150 mm wide and 175 mm long odor-controlling sheet B to make an absorbent member. The skin non-contacting surface side of the absorbent member is covered with the backsheet 3 of a liquid-impermeable and steam-permeable leakproof layer having a width of 100 mm and a length of 205 mm (prepared by dispersing calcium carbonate particles in polyethylene, forming the dispersion into a film, and stretching the film). A 100 mm wide and 205 mm long liquid permeable top layer of perforated polyethylene film was laid over the skin-contacting surface side of the absorbent member. The leakproof layer and the top layer were heat-sealed at the longitudinal front and rear edges and the lateral edges of the absorbent member. Afterward, the same manner as in Example 1 was repeated to obtain a sanitary napkin.

Example 6

A sanitary napkin was obtained in the same manner as in Example 5, except for replacing the odor-controlling sheet B with the odor-controlling sheet C.

Comparative Example 4

A sanitary napkin was obtained in the same manner as in Example 5, except for replacing the odor-controlling sheet B with the absorbent sheet G.

The odor-controlling performance of the sanitary napkins obtained in Examples and Comparative Examples was evaluated as follows. Further, the dry, wet, and combined odor-controlling abilities of the napkins against ammonia, methyl mercaptan, diethylamine, and acetic acid were measured according to the above-described methods. The results obtained are shown in Tables 2 through 4. In Tables 2 to 4, the figures representing odor concentrations that are not in parentheses are values measured at 25° C., and those in parentheses are values measured at 40° C.

1) Evaluation on Odor-Controlling Performance-1

Each of the sanitary napkins obtained in Examples 1 to 4 and Comparative Examples 1 to 3 was applied to a movable model of female hips and crotch by use of sanitary panties. The model was made to take a walking movement at a rate of 100 steps/min (corresponding to a walking speed of 50 m/min). While keeping the model in a moving mode, 5 mL of a solution of 100 μL of diethylamine in 5 mL of physiological saline was poured into the sanitary napkin, and the walking movement was continued for an additional 30 minute period at the same speed. The napkin was removed and subjected to evaluation. Randomly selected 25 testers were asked to smell the test sample about 10 cm away from their nose with the surface side facing the tester and to rate the odor according to the following standard. The points given by the 25 testers were added up and averaged. The smaller the point, the less the odor, indicating higher odor-controlling effects.

The sanitary napkins obtained in Examples 5 and 6 and Comparative Example 4 were evaluated in the same manner as described above, except that the testers were asked to smell the sample as being put on the sanitary panties from a distance of about 10 cm.

Standard of Evaluation:
1 . . . No odor is perceived.
2 . . . Slight odor is perceived but won't bother.
3 . . . Slightly unpleasant odor is perceived.
4 . . . An unpleasant odor is perceived.

2) Evaluation on Odor-Controlling Performance-2

25 female testers who were sensitive to smell during menstruation were chosen based on the results of a consciousness survey carried out beforehand. Each tester was asked to use the napkins prepared in Examples 1 to 4 and Comparative Examples 1 to 3 (four napkins per kind). Two out of the four napkins per kind were used on heavy days (days of heavy bleeding in her period, usually the first to third days), and the rest on light days (days of slight bleeding, usually from the fourth days on). The napkins were used for at least 2 hours each. The testers were asked to smell in the following situations and to rate the odor based on the same standard as in Evaluation (1).

2-1) On Heavy Days
  (a) When 1 hour or more has passed after putting on the napkin and while the napkin is being worn.
  (b) When the napkin is removed.

2-2) On Light Days
  (a) When 1 hour or more has passed after putting on the napkin and while the napkin is being worn.
  (b) When the napkin is removed.

TABLE 2

| | | Example 1 | | Example 2 | | Example 3 | | Example 4 | |
|---|---|---|---|---|---|---|---|---|---|
| | | Odor-Controlling Sheet | | | | | | | |
| | | A | | B | | C | | D | |
| | | Time of Measurement | | | | | | | |
| | | After 30 mins | After 3 hrs | After 30 mins | After 3 hrs | After 30 mins | After 3 hrs | After 30 mins | After 3 hrs |
| Dry Odor-Controlling Ability (ppm) | Ammonia | 0 (4) | 0 (1) | 0 (5) | 0 (0) | 0 (5) | 0 (1) | 0 (5) | 0 (0) |
| | Methyl Mercaptan | 3 (5) | 0 (1) | 3 (5) | 0 (1) | 0 (5) | 0 (1) | 0 (5) | 0 (0) |

TABLE 2-continued

| | | Example 1 | | Example 2 | | Example 3 | | Example 4 | |
|---|---|---|---|---|---|---|---|---|---|
| | | Odor-Controlling Sheet | | | | | | | |
| | | A | | B | | C | | D | |
| | | Time of Measurement | | | | | | | |
| | | After 30 mins | After 3 hrs | After 30 mins | After 3 hrs | After 30 mins | After 3 hrs | After 30 mins | After 3 hrs |
| Wet Odor-Controlling Ability (ppm) | Amine | 7 (15) | 0 (0) | 6 (10) | 0 (0) | 2 (15) | 0 (0) | 5 (15) | 0 (0) |
| | Acetic Acid | 5 (10) | 1 (2) | 4 (7) | 1 (2) | 5 (10) | 1 (1) | 5 (7) | 1 (2) |
| | Ammonia | 10 (15) | 3 (5) | 5 (15) | 0 (3) | 8 (13) | 1 (3) | 5 (13) | 0 (3) |
| | Methyl Mercaptan | 4 (7) | 1 (2) | 1 (5) | 0 (0) | 3 (8) | 1 (2) | 2 (7) | 1 (1) |
| Combined Odor-controlling Ability (ppm) | Amine | 6 (10) | 0 (0) | 5 (5) | 0 (0) | 7 (10) | 0 (1) | 5 (10) | 0 (1) |
| | Acetic Acid | 2 (7) | 0 (1) | 1 (5) | 0 (1) | 2 (5) | 0 (1) | 2 (5) | 0 (1) |
| | Ammonia | 15 (17) | 3 (7) | 10 (17) | 0 (5) | 15 (20) | 1 (7) | 10 (15) | 0 (2) |
| | Methyl Mercaptan | 7 (10) | 1 (2) | 6 (8) | 0 (1) | 12 (18) | 1 (2) | 8 (12) | 0 (1) |
| | Amine | 10 (15) | 2 (5) | 7 (15) | 1 (2) | 10 (15) | 2 (5) | 10 (15) | 1 (5) |
| | Acetic Acid | 7 (10) | 2 (3) | 6 (10) | 1 (2) | 7 (13) | 2 (3) | 6 (10) | 1 (2) |
| Odor-Controlling Performance-1 | | 1.5 | | 1.3 | | 1.4 | | 1.9 | |
| Odor-Controlling Performance-2 | Heavy Days While Worn | 1.5 | | 1.5 | | 1.6 | | 1.5 | |
| | Heavy Days On Removal | 1.7 | | 1.5 | | 1.9 | | 1.9 | |
| | Light Days While Worn | 1.3 | | 1.2 | | 1.4 | | 1.5 | |
| | Light Days On Removal | 1.5 | | 1.3 | | 1.5 | | 1.6 | |

Note:
Values in parentheses are values measured at 40° C.

TABLE 3

| | | Compara. Example 1 | | Compara. Example 2 | | Compara. Example 3 | |
|---|---|---|---|---|---|---|---|
| | | Odor-Controlling Sheet | | | | | |
| | | E | | F | | — | |
| | | Time of Measurement | | | | | |
| | | After 30 mins | After 3 hrs | After 30 mins | After 3 hrs | After 30 mins | After 3 hrs |
| Dry Odor-Controlling Ability (ppm) | Ammonia | 10 (15) | 0 (3) | 15 (20) | 0 (2) | 20 (30) | 18 (30) |
| | Methyl Mercaptan | 7 (10) | 1 (2) | 7 (10) | 1 (2) | 40 (50) | 40 (50) |
| | Amine | 10 (15) | 0 (2) | 15 (20) | 1 (3) | 50 (80) | 50 (70) |
| | Acetic Acid | 7 (10) | 3 (5) | 8 (14) | 3 (5) | 10 (17) | 4 (5) |
| Wet Odor-Controlling Ability (ppm) | Ammonia | 28 (50) | 10 (30) | 30 (50) | 7 (25) | 80 (130) | 20 (150) |
| | Methyl Mercaptan | 15 (30) | 12 (30) | 15 (30) | 10 (25) | 50 (80) | 50 (80) |
| | Amine | 30 (70) | 5 (20) | 30 (70) | 7 (20) | 100 (200) | 70 (120) |
| | Acetic Acid | 15 (30) | 6 (12) | 15 (30) | 5 (12) | 20 (42) | 15 (30) |
| Combined Odor-Controlling Ability (ppm) | Ammonia | 35 (60) | 10 (20) | 45 (70) | 15 (30) | 100 (150) | 100 (120) |
| | Methyl Mercaptan | 50 (70) | 40 (70) | 50 (70) | 40 (70) | 70 (90) | 70 (80) |
| | Amine | 50 (70) | 10 (30) | 50 (70) | 15 (30) | 100 (180) | 100 (150) |

TABLE 3-continued

|  |  |  | Compara. Example 1 | | Compara. Example 2 | | Compara. Example 3 | |
| --- | --- | --- | --- | --- | --- | --- | --- | --- |
|  |  |  | Odor-Controlling Sheet | | | | | |
|  |  |  | E | | F | | — | |
|  |  |  | Time of Measurement | | | | | |
|  |  |  | After 30 mins | After 3 hrs | After 30 mins | After 3 hrs | After 30 mins | After 3 hrs |
|  | Acetic acid |  | 20 (30) | 10 (19) | 25 (35) | 10 (22) | 30 (45) | 15 (20) |
| Odor-Controlling Performance-1 |  |  | 3.4 | | 3.6 | | 3.8 | |
| Odor-Controlling Performance-2 | Heavy Days | While Worn | 2.7 | | 2.2 | | 2.9 | |
|  |  | On Removal | 3.3 | | 3.3 | | 4.0 | |
|  | Light Days | While Worn | 2.2 | | 2.5 | | 3.2 | |
|  |  | On Removal | 2.7 | | 2.9 | | 3.5 | |

Note:
The values in parentheses are as measured at 40° C.

TABLE 4

|  |  | Example 5 | | Example 6 | | Example 7 | |
| --- | --- | --- | --- | --- | --- | --- | --- |
|  |  | Odor-Controlling Sheet | | | | | |
|  |  | B | | C | | Absorbent Sheet G | |
|  |  | Time of Measurement | | | | | |
|  |  | After 30 mins | After 3 hrs | After 30 mins | After 3 hrs | After 30 mins | After 3 hrs |
| Dry Odor-Controlling Ability (ppm) | Ammonia | 0 (4) | 0 (0) | 0 (5) | 0 (0) | 20 (30) | 18 (30) |
|  | Methyl Mercaptan | 3 (5) | 0 (1) | 3 (5) | 0 (1) | 40 (50) | 40 (50) |
|  | Amine | 6 (10) | 0 (0) | 6 (10) | 0 (0) | 50 (90) | 50 (70) |
|  | Acetic Acid | 5 (10) | 1 (2) | 5 (10) | 1 (2) | 10 (19) | 4 (5) |
| Wet Odor-Controlling Ability (ppm) | Ammonia | 8 (15) | 0 (3) | 8 (13) | 1 (2) | 100 (200) | 80 (120) |
|  | Methyl Mercaptan | 2 (5) | 1 (2) | 3 (5) | 1 (2) | 50 (80) | 50 (80) |
|  | Amine | 7 (15) | 0 (1) | 7 (18) | 1 (2) | 100 (200) | 70 (120) |
|  | Acetic Acid | 2 (5) | 0 (1) | 1 (5) | 0 (2) | 20 (40) | 15 (20) |
| Combined Odor-Controlling Ability (ppm) | Ammonia | 15 (20) | 3 (6) | 15 (16) | 1 (3) | 100 (200) | 100 (150) |
|  | Methyl Mercaptan | 8 (10) | 0 (1) | 12 (16) | 2 (3) | 70 (100) | 70 (80) |
|  | Amine | 10 (15) | 2 (5) | 10 (15) | 2 (7) | 100 (180) | 100 (150) |
|  | Acetic acid | 7 (13) | 3 (15) | 7 (15) | 3 (5) | 30 (50) | 15 (25) |
| Odor-Controlling Performance-1 |  | 1.4 | | 1.5 | | 3.8 | |
| Odor-Controlling Performance-2 Heavy Days While Worn |  | 2.1 | | 2.0 | | 3.4 | |
| On Removal |  | 1.7 | | 1.5 | | 4.0 | |
| Light Days While Worn |  | 1.8 | | 1.9 | | 3.4 | |
| On Removal |  | 1.3 | | 1.5 | | 3.8 | |

Note:
The values in parentheses are as measured at 40° C.

As is apparent from the results shown in Tables 2 to 4, the sanitary napkins of Examples 1 to 6 according to the present invention exhibit higher odor-controlling effects than those of Comparative Examples 1 to 4, controlling bad odors below perceptible levels or bothering levels. In particular, the sanitary napkins of Examples 1 to 6 show excellent odor-controlling ability in the wet state and the dry/wet combined state, whereas these Comparative Examples 1 to 4 are considerably inferior in these attributes.

Since the odor-controlling sheets A to D used in the articles of the invention comprise hydrophilic fiber that does not swell with water or that has a specific centrifugal water retention, body fluids containing bad odor components quickly migrate toward the odor-controlling agent and the superabsorbent polymer without staying in the interstices among fibers. The fluids are absorbed and fixed by the odor-controlling agent and the superabsorbent polymer so that development of bad odors is prevented effectively.

Because the absorbent members of Examples 1 and 2 are both made of the above-described odor-controlling sheets, the sanitary napkins in these Examples achieve efficient odor control. In Examples 3 and 4, because the absorbent members have chemical pulp in their central portion, the absorbed liquid may stay there to develop bad odors. However, with the central portion being enveloped in the odor-controlling sheet, the bad odors developed are controlled without fail while passing through the odor-controlling sheet. In Examples 5 and 6 where the steam-permeable sheet is used as a leakproof layer, the sanitary napkins are comfortable to use because of the breathability. Additionally, progress of bacterial decomposition of the absorbed liquid, which leads to increase of bad odors, is minimized in the absence of increased humidity. Although bad odors could dissipate into the air through the leakproof layer, they always pass through the odor-controlling sheet where they are controlled.

On the other hand, the odor-controlling sheets used in Comparative Examples 1 and 2, which do not comprise the above-described specific fiber, fail to make effective use of the odor-controlling agent. As a result, the articles have inferior odor-controlling effects, allowing the bad odors developed to be perceived by the wearer.

As described above, the present invention provides absorbent articles which have high odor-controlling effects and are resistant to leakage of bad odors.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An absorbent article comprising a liquid permeable top layer, a liquid impermeable leakproof layer, and a liquid retentive absorbent layer disposed there between, wherein said liquid retentive absorbent layer comprises an odor-controlling member containing components (a), (b) and (c):
   (a) a synthetic hydrophilic fiber having an average fiber diameter of 0.1 to 10 μm that does not swell with water, or a crosslinked cellulose fiber that has a centrifugal water retention of 0.7 g/g or less as measured after equilibrium water absorption and swelling followed by centrifugation,
   (b) an odor-controlling agent and
   (c) a superabsorbent polymer, and
   wherein said odor-controlling member contains a layer or web of component (a) having dispersed therein said superabsorbent polymer (c), wherein the odor-controlling agent (b) is fixedly adhered to the component (a) layer via the superabsorbent polymer (c);
   wherein said odor-controlling member is an odor-controlling sheet comprising 20 to 80% by weight of said component (a), 10 to 60% by weight of said component (b), and 10 to 60% by weight of said component (c) superabsorbent polymer, and
   wherein said odor-controlling sheet has a Klemm's water absorption at 1 minute of 40 mm or more as measured according to JIS P 8141 using physiological saline.

2. An absorbent article used for body fluid absorption wherein, in tests which are carried out by introducing the following liquids into 900 mL glass containers respectively, immediately after the liquid introduction putting said absorbent articles into glass containers respectively, closing the glass containers tightly, and maintaining the closed glass containers at 25° C., said absorbent article is capable of reducing the concentration of:
   ammonia gas to less than 10 ppm in 30 minutes and to 5 ppm or less in 3 hours in the case of introducing 0.1 μL of 29% by weight of an aqueous ammonia, and
   methyl mercaptan gas to 20 ppm or less in 30 minutes and to 2 ppm or less in 3 hours in the case of introducing 100 μL of a 1 μg/μL benzene solution of methyl mercaptan; and
   wherein, in tests which are carried out by applying the following liquids to said absorbent articles respectively, immediately thereafter putting said absorbent articles into 900 mL glass containers respectively, closing the glass containers tightly, and maintaining the closed glass containers at 25° C., said absorbent article is capable of reducing the concentration of:
   ammonia gas to 20 ppm or less in 30 minutes and to 7 ppm or less in 3 hours in the case of applying 60 μL of 29% by weight of an aqueous ammonia and 5 mL of physiological saline in this order to the same portion of said absorbent article, and
   methyl mercaptan gas to 20 ppm or less in 30 minutes and to 2 ppm or less in 3 hours in the case of applying 100 μL of a 1 μg/μL benzene solution of methyl mercaptan and 5 mL of physiological saline in this order to the same portion of said absorbent article; and
   wherein said absorbent article has an absorbent layer comprising an odor-controlling member containing components (a), (b) and (c):
   (a) a synthetic hydrophilic fiber having an average fiber diameter of 0.1 to 10 μm that does not swell with water, or a crosslinked cellulose fiber that has a centrifugal water retention of 0.7 g/g or less as measured after equilibrium water absorption and swelling followed by centrifugation,
   (b) an odor-controlling agent and
   (c) a superabsorbent polymer,
   wherein the proportion of component (a) in said odor-controlling member being 20 to 80% by weight;
   wherein said odor-controlling member contains a layer or web of component (a) having dispersed therein said superabsorbent polymer (c), wherein the odor-controlling agent (b) is fixedly adhered to the component (a) layer via the superabsorbent polymer (c);
   wherein said odor-controlling sheet has a Klemm's water absorption at 1 minute of 40 mm or more as measured according to JIS P 8141 using physiological saline.

3. An absorbent article used for body fluid absorption as recited in claim 2, wherein said absorbent article is capable of reducing the concentration of:

ammonia gas to 10 ppm or less in 30 minutes and to 5 ppm or less in 3 hours in the case that 0.1 μL of 29% by weight of an aqueous ammonia is introduced into the glass container, and that said absorbent article has previously absorbed 60 μL of 29% by weight of an aqueous ammonia and 5 mL of physiological saline in this order in the same portion thereof; and methyl mercaptan gas to 10 ppm or less in 30 minutes and to 2 ppm or less in 3 hours in the case that 100 μL of a 1 μg/μL benzene solution of methyl mercaptan is introduced into the glass container, and that said absorbent article has previously absorbed 100 μL of a 1 μg/μL benzene solution of methyl mercaptan and 5 mL of physiological saline in this order in the same portion thereof.

4. The absorbent article according to claim 1, wherein said odor-controlling member contains a binder.

5. An absorbent article comprising a liquid permeable top layer, a liquid impermeable leakproof layer, and a liquid retentive absorbent layer disposed there between, wherein said absorbent layer has an odor-controlling member containing (a) a synthetic hydrophilic fiber having an average fiber diameter of 0.1 to 10 μm that does not swell with water, or a crosslinked cellulose fiber that has a centrifugal water retention of 0.7 g/g or less as measured after equilibrium water absorption and swelling followed by centrifugation, (b) an odor-controlling agent and (c) a superabsorbent polymer, and said odor-controlling member being composed of a layer or web of component (a) having dispersed therein said superabsorbent polymer (c), wherein the odor-controlling agent (b) is fixedly adhered to the component (a) layer via the superabsorbent polymer (c);

wherein component (a) is present in an amount of 5 to 70% by weight and component (b) is present in an amount of 5 to 70% by weight, based on the total weight of the absorbent layer and the weight proportion of the odor-controlling member in the total absorbent layer is 10% by weight or more, wherein said odor-controlling member is an odor-controlling sheet comprising 20 to 80% by weight of said component (a), 10 to 60% by weight of said component (b), and 10 to 60% by weight of said component (c) superabsorbent polymer, and wherein said odor-controlling sheet has a Klemm's water absorption at 1 minute of 40 nm or more as measured according to JIS P 8141 using physiological saline.

6. The absorbent article according to claim 1, wherein said absorbent article is a sanitary napkin.

7. The absorbent article according to claim 1, wherein said absorbent article is a panty liner.

8. The absorbent article according to claim 2, wherein said absorbent article is a sanitary napkin.

9. The absorbent article according to claim 2, wherein said absorbent article is a panty liner.

10. The absorbent article according to claim 1, wherein the liquid impermeable leakproof layer is permeable to steam.

11. The absorbent article according to claim 10, wherein the odor-controlling member of the absorbent layer is disposed in contact with the leakproof layer.

12. The absorbent article comprising a liquid permeable top layer according to claim 1, wherein upon folding the odor-controlling member into a C-shaped closed sheet, the component (b) odor-controlling agent is on the outside of the odor-controlling member relative to the component (c) superabsorbent polymer.

13. The absorbent article used for body fluid absorption according to claim 2, wherein upon folding the odor-controlling member into a C-shaped closed sheet, the component (b) odor-controlling agent is on the outside of the odor-controlling member relative to the component (c) superabsorbent polymer.

14. The absorbent article comprising a liquid permeable top layer according to claim 5, wherein upon folding the odor-controlling member into a C-shaped closed sheet, the component (b) odor-controlling agent is on the outside of the odor-controlling member relative to the component (c) superabsorbent polymer.

15. An absorbent article comprising a liquid permeable top layer, a liquid impermeable leakproof layer that is permeable to steam, and a liquid retentive absorbent layer disposed there between, wherein said absorbent layer has an odor-controlling member containing (a) a synthetic hydrophilic fiber having an average fiber diameter of 0.1 to 10 μm that does not swell with water, or a crosslinked cellulose fiber that has a centrifugal water retention of 0.7 g/g or less as measured after equilibrium water absorption and swelling followed by centrifugation, (b) an odor-controlling agent and (e) a superabsorbent polymer;

wherein said odor-controlling member being composed of a layer or web of component (a) having dispersed therein said superabsorbent polymer (c), wherein the odor-controlling agent (b) is fixedly adhered to the component (a) layer via the superabsorbent polymer (c);

wherein said odor-controlling member is an odor-controlling sheet comprising 20 to 80% by weight of said component (a), 10 to 60% by weight of said component (b), and 10 to 60% by weight of said component (c) superabsorbent polymer, and wherein said odor-controlling sheet has a Klemm's water absorption at 1 minute of 40 mm or more as measured according to JIS P 8141 using physiological saline.

16. The absorbent article comprising a liquid permeable top layer according to claim 15, wherein upon folding the odor-controlling member into a C-shaped closed sheet, the component (b) odor-controlling agent is on the outside of the odor-controlling member relative to the component (c) superabsorbent polymer.

17. The absorbent article according to claim 1, wherein said odor-controlling sheet comprises from 40 to 80% by weight of said component (a).

18. The absorbent article according to claim 2 wherein said odor-controlling sheet comprises from 40 to 80% by weight of said component (a).

19. The absorbent article according to claim 5 wherein said odor-controlling sheet comprises from 40 to 80% by weight of said component (a).

20. The absorbent article according to claim 15 wherein said odor-controlling sheet comprises from 40 to 80% by weight of said component (a).

21. The absorbent article according to claim 1, wherein component (a) comprises a synthetic hydrophilic fiber having an average fiber diameter of 0.1 to 10 μm that does not swell with water.

22. The absorbent article according to claim 2, wherein component (a) comprises a synthetic hydrophilic fiber having an average fiber diameter of 0.1 to 10 μm that does not swell with water.

23. The absorbent article according to claim 5, wherein component (a) comprises a synthetic hydrophilic fiber having an average fiber diameter of 0.1 to 10 μm that does not swell with water.

24. The absorbent article according to claim 15, wherein component (a) comprises a synthetic hydrophilic fiber having an average fiber diameter of 0.1 to 10 μm that does not swell with water.

25. The absorbent article according to claim 1, wherein said component (a) comprises a crosslinked cellulose fiber that has a centrifugal water retention of 0.7 g/g or less as measured after equilibrium water absorption and swelling followed by centrifugation.

26. The absorbent article according to claim 2, wherein said component (a) comprises a crosslinked cellulose fiber that has a centrifugal water retention of 0.7 g/g or less as measured after equilibrium water absorption and swelling followed by centrifugation.

27. The absorbent article according to claim 5, wherein said component (a) comprises a crosslinked cellulose fiber that has a centrifugal water retention of 0.7 g/g or less as measured after equilibrium water absorption and swelling followed by centrifugation.

28. The absorbent article according to claim 15, wherein said component (a) comprises a crosslinked cellulose fiber that has a centrifugal water retention of 0.7 g/g or less as measured after equilibrium water absorption and swelling followed by centrifugation.

* * * * *